United States Patent
Yamamoto et al.

(10) Patent No.: US 11,631,160 B2
(45) Date of Patent: Apr. 18, 2023

(54) IMAGE PROCESSING APPARATUS, IMAGE PROCESSING METHOD, AND X-RAY CT APPARATUS

(71) Applicant: Hitachi, Ltd., Tokyo (JP)

(72) Inventors: Mariko Yamamoto, Tokyo (JP); Keisuke Yamakawa, Tokyo (JP); Isao Takahashi, Tokyo (JP); Taiga Gotou, Tokyo (JP); Hisashi Takahashi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 58 days.

(21) Appl. No.: 16/897,768

(22) Filed: Jun. 10, 2020

(65) Prior Publication Data

US 2021/0027430 A1     Jan. 28, 2021

(30) Foreign Application Priority Data

Jul. 25, 2019 (JP) .............................. JP2019-136899

(51) Int. Cl.
*G06T 5/00* (2006.01)
*G06T 7/00* (2017.01)

(52) U.S. Cl.
CPC ............ *G06T 5/002* (2013.01); *G06T 7/0012* (2013.01); *G06T 2207/10081* (2013.01);
(Continued)

(58) Field of Classification Search
CPC ................... G06T 5/002; G06T 7/0012; G06T 2207/10081; G06T 2207/10116;
(Continued)

(56) References Cited

U.S. PATENT DOCUMENTS

2012/0213327 A1*  8/2012  Boas .................... G06T 11/005
                                                                 378/5
2013/0051516 A1*  2/2013  Yang .................... G06T 11/005
                                                                 378/4

(Continued)

OTHER PUBLICATIONS

L. Gjesteby, et al., "Metal Artifact Reduction in CT: Where are we after four decades?", IEEE Access, vol. 4, Sep. 13, 2016, pp. 5826-5849.

(Continued)

*Primary Examiner* — Vu Le
*Assistant Examiner* — Winta Gebreslassie
(74) *Attorney, Agent, or Firm* — Mattingly & Malur, PC

(57) ABSTRACT

Noise is reduced for a medical image for which noise cannot be quantified by a general-purpose image quality evaluation index. An image processor has a preprocessor that generates input images including an original image and one or more images with reduced noise compared with the original image; and a noise reduction processor outputs an image, which is obtained by reducing noise from the original image based on the input images, by applying a learned network. The learned network used in the noise reduction processor is constructed by performing deep learning using a plurality of learning sets in which one or more of a medical image including noise, a noise-reduced image obtained by performing noise reduction processing on the medical image, and an intermediate image obtained during the noise reduction processing are input images and a correct image is obtained based on the input images an output image.

5 Claims, 12 Drawing Sheets

(52) U.S. Cl.
CPC ........... *G06T 2207/10116* (2013.01); *G06T 2207/30008* (2013.01); *G06T 2207/30024* (2013.01)

(58) Field of Classification Search
CPC . G06T 2207/30008; G06T 2207/30024; G06T 5/50; G06T 2207/22081; G06T 11/008; G06T 11/005; G06T 2207/20021; G06T 2207/30136; G06T 9/002
See application file for complete search history.

(56) References Cited

U.S. PATENT DOCUMENTS

| | | | |
|---|---|---|---|
| 2017/0000443 A1* | 1/2017 | Katsumata | A61B 6/5282 |
| 2019/0244399 A1* | 8/2019 | Li | G01R 33/56545 |
| 2019/0325621 A1* | 10/2019 | Wang | G06N 3/0472 |
| 2019/0328348 A1* | 10/2019 | De Man | G06T 11/008 |
| 2021/0104313 A1* | 4/2021 | Mizobe | G06T 5/002 |

OTHER PUBLICATIONS

Zach Eaton-Rosen, et al. "Improving Data Augmentation for Medical Image Segmentation", 1st Conference on Medical Imaging with Deep Learning (MIDL 2018), Amsterdam, The Netherlands.

* cited by examiner

FIG. 11

| PURPOSE | | CONVERSION NUMBER K |
|---|---|---|
| IMAGING PART | IMAGING TISSUE | |
| HEAD | BONE | 1 |
| | SOFT PART | 2 |
| JAW | BONE | 3 |
| | SOFT PART | 4 |
| LUMBAR SPINE | BONE | 7 |
| | SOFT PART | 8 |
| HIP JOINT | BONE | 9 |
| | SOFT PART | 9 |
| KNEE | BONE | 10 |
| | SOFT PART | 11 |
| SHOULDER | BONE | 10 |
| | SOFT PART | 11 |
| ... | ... | ... |

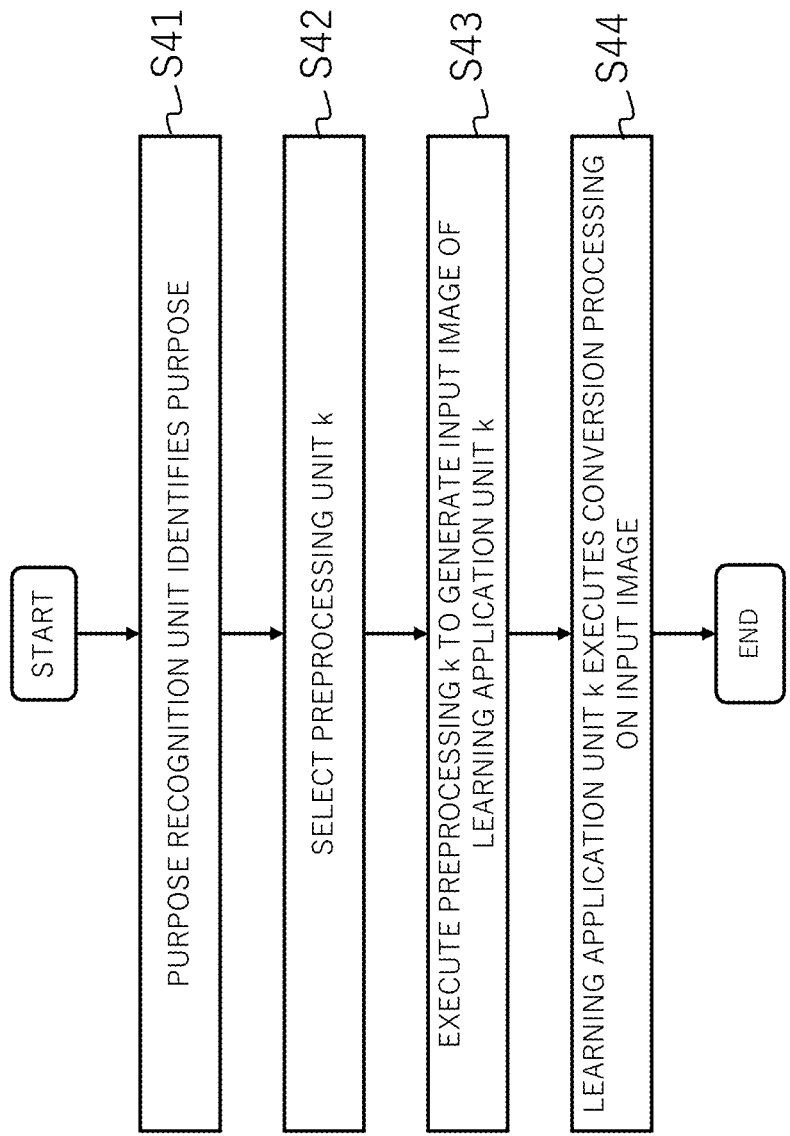

IMAGE PROCESSING APPARATUS, IMAGE PROCESSING METHOD, AND X-RAY CT APPARATUS

CROSS-REFERENCE TO RELATED APPLICATION

The present application claims priority from Japanese application JP2019-136899, filed on Jul. 25, 2019, the contents of which is hereby incorporated by reference into this application.

BACKGROUND OF THE INVENTION

Field of the Invention

The present invention relates to an image processing apparatus, an image processing method, and an X-ray CT apparatus and in particular, to an image processing apparatus, an image processing method, and an X-ray CT apparatus for reducing image noise using machine learning or deep learning.

Description of the Related Art

Medical images captured by an X-ray CT apparatus have different definitions of signal and noise depending on the purpose of the image. Accordingly, there is a feature that images with clinically necessary accuracy cannot be generated by simulation and noise cannot be quantified by a general-purpose image quality evaluation index. In addition, there are various methods for the noise reduction processing. For example, processing for reducing noise caused by metal can be classified into three types of (1) processing in a real space, (2) processing in a projection space, and (3) repetition processing of a combination thereof (Gjesteby, L., et al. (2016). "Metal Artifact Reduction in CT: Where are we after four decades?", IEEE Access, 4, 5826-5849). The noise reduction effect and the calculation cost of these processes are larger in the process (2) than in the process (1) and larger in the process (3) than in the process (2). The processing (3) can theoretically reduce the noise to zero, but is not adopted in a commercial machine that requires a high throughput because of high calculation cost. The processes (1) and (2) are adopted in commercial machines, and are used depending on the purpose of the image.

On the other hand, for general images, noise reduction processing using machine learning or deep learning is highly effective as an adaptive filter that adaptively evaluates an image and performs noise reduction according to the feature of the image (Z. Eaton-Rosen, et al. "Improving Data Augmentation for Medical Image Segmentation", MIDL 2018).

Machine learning or deep learning cannot be quantified by a general-purpose image quality evaluation index, and is expected as a method for reducing the noise of a medical image that requires adaptive processing depending on the purpose. However, the application itself of the method is difficult. This is because, when trying to construct a learned network using a noise-free image as a correct image as is customary in deep learning for general images, no correct image is present or the absolute number of correct images is small even though the correct images are present, and accordingly, the number of correct images required for deep learning cannot be satisfied (Z. Eaton-Rosen, et al. "Improving Data Augmentation for Medical Image Segmentation", MIDL 2018).

SUMMARY OF THE INVENTION

The invention has been made in view of the above circumstances, and it is an object of the invention to improve image quality by accurately reducing noise even for a medical image for which noise cannot be quantified by a general-purpose image quality evaluation index.

In order to solve the aforementioned problems, the invention provides the following means.

According to an aspect of the invention, there is provided an image processing apparatus including: a preprocessing unit that generates input images including an original image and one or more images with reduced noise compared with the original image; and a noise reduction processing unit that outputs an image, which is obtained by reducing noise from the original image based on the input images, by applying a learned network. The learned network used in the noise reduction processing unit is constructed by performing deep learning using a plurality of learning sets in which one or more of a medical image including noise, a noise-reduced image obtained by performing noise reduction processing on the medical image, and an intermediate image obtained during the noise reduction processing are input images and a correct image obtained based on the input images is an output image.

According to another aspect of the invention, there is provided an image processing method including: a preprocessing step for generating input images including an original image and one or more images with reduced noise compared with the original image; and a noise reduction processing step for outputting an image, which is obtained by reducing noise from the original image based on the input images, by applying a learned network. The learned network used in the noise reduction processing step is constructed by performing deep learning using a plurality of learning sets in which one or more of a medical image including noise, a noise-reduced image obtained by performing noise reduction processing on the medical image, and an intermediate image obtained during the noise reduction processing are input images and a correct image obtained based on the input images is an output image.

According to still another aspect of the invention, there is provided an X-ray CT apparatus including: an imaging unit that emits X-rays to a subject and detects X-rays transmitted through the subject to generate an image; and the image processing apparatus described above. The image processing apparatus performs noise reduction processing using the image generated by the imaging unit as an original image.

According to the invention, it is possible to improve image quality by accurately reducing noise even for a medical image for which noise cannot be quantified by a general-purpose image quality evaluation index.

BRIEF DESCRIPTION OF THE DRAWINGS

FIG. 11 is a correspondence table showing an example of a correspondence relationship between a purpose and a process associated with a conversion number in the second embodiment of the invention; and FIG. 12 is a flowchart showing the flow of noise reduction processing performed by the image processing unit (image processing apparatus) according to the second embodiment of the invention.

DETAILED DESCRIPTION OF THE INVENTION

First Embodiment

Hereinafter, an X-ray CT apparatus to which an image processing apparatus (image processing unit) according to a first embodiment of the invention is applied will be described with reference to the accompanying diagrams.

Figure 1:
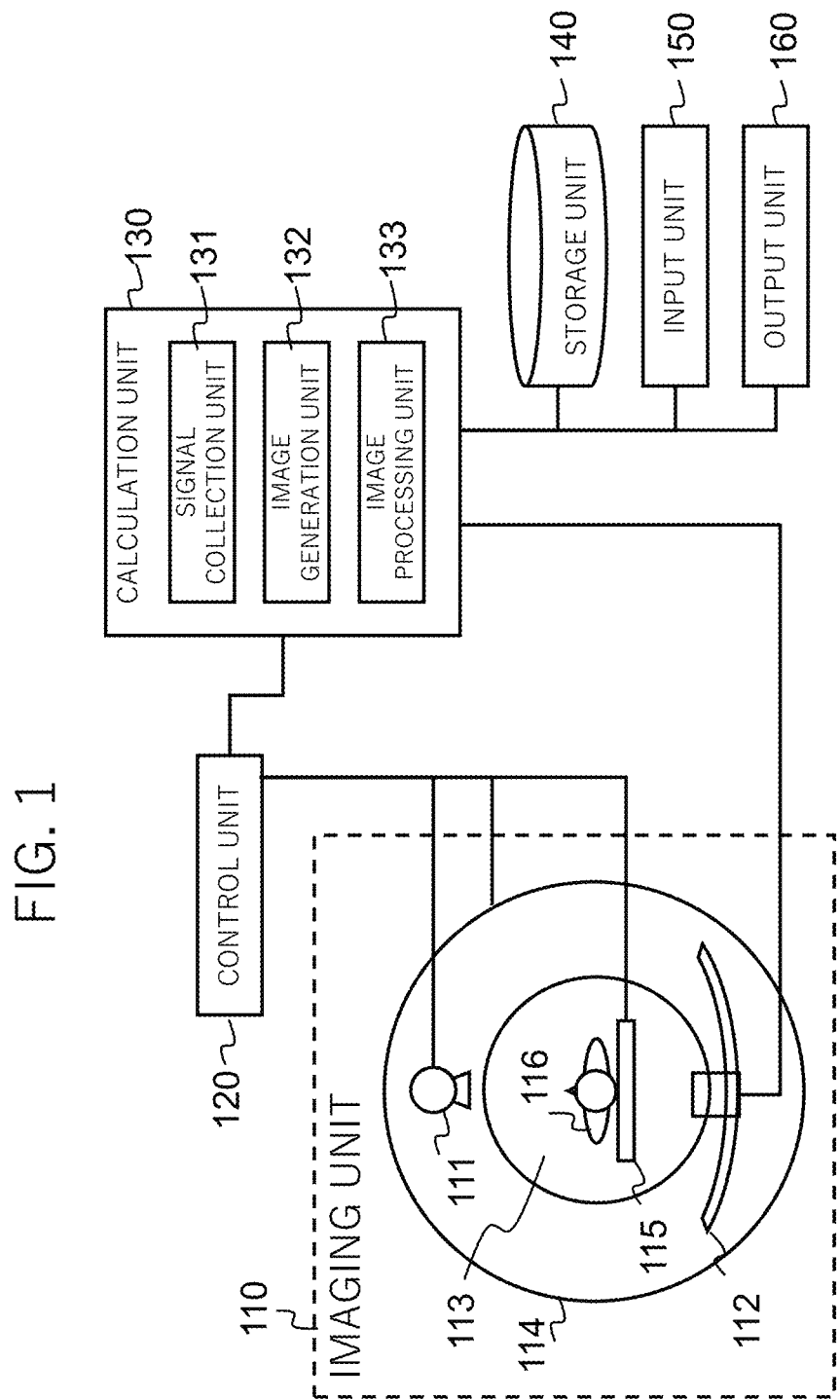
FIG. 1 is a block diagram showing a schematic configuration of an X-ray CT apparatus to which an image processing apparatus according to a first embodiment of the invention is applied.

FIG. 1 shows a schematic configuration diagram of the X-ray CT apparatus according to the present embodiment. The X-ray CT apparatus shown in FIG. 1 includes an imaging unit 110 that performs X-ray irradiation and detection, a control unit 120 that controls the imaging of the imaging unit 110, a calculation unit 130 that generates an image from a signal detected by the imaging unit 110 and performs predetermined processing, a storage unit 140 that stores a program executed by the calculation unit 130 or data required to execute the program, an input unit 150 for inputting imaging conditions, such as X-ray irradiation conditions, or image generation conditions, and an output unit 160 for displaying a generated image.

The imaging unit 110 includes an X-ray source 111 having an X-ray tube, an X-ray detector 112 in which a plurality of X-ray detection elements are arranged in a one-dimensional or two-dimensional manner, a rotating disk 114 in which the X-ray source 111 and the X-ray detector 112 are disposed and supported so as to face each other and which has an opening 113 at the center, a table 115 that is located inside the opening 113 and is movable in a normal direction of the opening surface.

The control unit 120 includes a controller provided for each component included in the imaging unit 110, such as an X-ray controller, a rotating disk controller, and a table controller (not shown), and a necessary control signal is transmitted to the imaging unit 110 by loading and executing a predetermined program in the calculation unit 130 described later.

The calculation unit 130 performs overall control of the X-ray CT apparatus, and transmits a necessary signal to each controller included in the control unit 120. In addition, the calculation unit 130 collects an X-ray detection signal received from the imaging unit 110 to generate a reconstructed image, and performs predetermined image processing on the reconstructed image. The calculation unit 130 can be configured by a CPU (Central Processing Unit), a GPU (Graphics Processing Unit), or a combination of both.

The calculation unit 130 realizes the functions of a signal collection unit 131, an image generation unit 132, and an image processing unit 133. Some or all of the operations performed by the respective units included in the calculation unit 130 can be realized by an ASIC (application specific integrated circuit) or an FPGA (field-programmable gate array).

The signal collection unit 131 collects an analog X-ray detection signal received from the X-ray detector 112 and converts the analog X-ray detection signal into a digital projection signal. For example, a data acquisition system (DAS) can be applied. The image generation unit 132 generates a reconstructed image (CT image) based on the digital projection signal collected and converted by the signal collection unit 131. The image processing unit 133 performs predetermined image processing including noise reduction processing on the reconstructed image generated by the image generation unit 132. Details of the image processing unit 133 will be described later.

The storage unit 140 stores a program executed by the calculation unit 130, data required to execute the program, and a learned network required to perform noise reduction processing by machine learning in the image processing unit 133 described later. As the storage unit 140, a memory, an HDD (Hard Disk Drive) device, and the like can be applied. The input unit 150 receives an input of imaging conditions by the user, and a keyboard, a mouse, a touch panel, and the like can be applied. As the output unit 160, for example, a monitor that displays an image generated by the calculation unit 130 can be applied.

(About Image Processing Unit)

The image processing apparatus according to the present embodiment is provided in an X-ray CT apparatus as the image processing unit 133. The image processing unit 133 performs various kinds of image processing on the reconstructed image generated by the image generation unit 132, such as noise reduction processing, edge extraction, and contrast adjustment, according to the imaging target or purpose. In the present embodiment, the image processing unit 133 mainly performs noise reduction processing, and a description of other image processes will be omitted.

When the image processing unit 133 is provided in the calculation unit 130 as in the present embodiment, its function is implemented as software mounted on a CPU or a GPU as the calculation unit 130 or hardware, such as an ASIC or an FPGA. In particular, a learning application unit 311 that is a function of the image processing unit 133 can be implemented by using known software, such as Tensorflow (Google), Chainer (Preferred Network), and Theano (Universite device Montreal).

Figure 2:
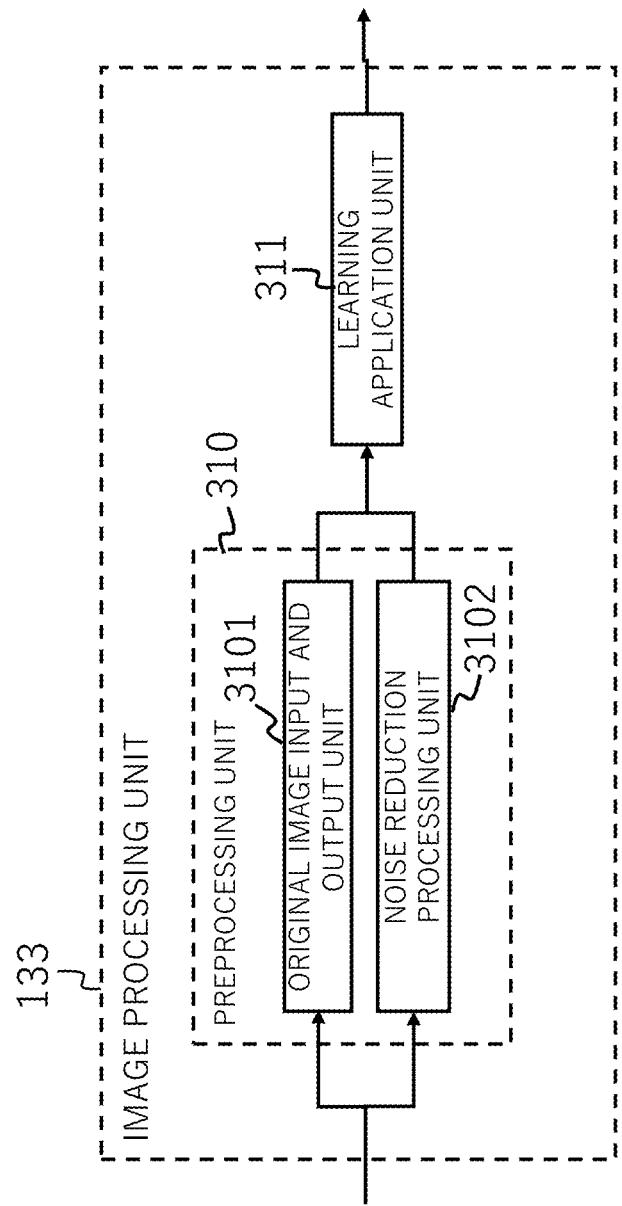
FIG. 2 is a block diagram showing a schematic configuration of an image processing unit (image processing apparatus) of the X-ray CT apparatus shown in FIG. 1.

In the present embodiment, the image processing unit 133 implements the noise reduction processing by machine learning or deep learning. Therefore, as shown in FIG. 2, the image processing unit 133 includes a preprocessing unit 310 and the learning application unit 311.

The preprocessing unit 310 generates an input image when the learning application unit 311 performs noise reduction processing by applying a deep learning network. The preprocessing unit 310 includes an original image input and output unit 3101 and a noise reduction processing unit 3102. The preprocessing unit 310 uses an original image input thereto as an input image, and generates at least one image (hereinafter, referred to as a "noise-reduced image"), which is obtained by performing known noise reduction processing on the original image, as an input image.

Specifically, the original image input and output unit 3101 outputs a reconstructed image (original image) received from the image generation unit 132 to the learning application unit 311 as an input image. In addition, the noise reduction processing unit 3102 generates, as input images, for example, three types of images of an intermediate image generated when performing predetermined known first noise reduction processing, a first noise-reduced image obtained by performing the noise reduction processing, and a second noise-reduced image obtained by performing another known second noise reduction processing, and outputs these images to the learning application unit 311.

Therefore, a total of four input images are output from the preprocessing unit 310 to the learning application unit 311. In the preprocessing unit 310, it is desirable that the plurality of input images are images having different noise characteristics. For example, in the learned network, when performing processing for reducing noise caused by metal from an image including noise caused by metal, it is preferable that the preprocessing unit 310 generates, as noise-reduced images, a projection replacement processed image in which a component affected by metal is replaced in the projection space with a value that reduces the effect of the metal, a linearly interpolated image obtained by linearly interpolating the components affected by metal in the projection space, and an image obtained by performing beam hardening correction processing.

In addition, as intermediate images by the known noise reduction processing, images obtained by dividing the original image into regions, such as air, soft tissue, and bone tissue, and reducing a noise component for each region, such as setting the region of the air to 0 HU and setting the region of the soft tissue to 1000 HU, a high frequency image in which high frequency components of the original image are emphasized, and an edge image showing the magnitude of the difference in pixel value between adjacent pixels in the original image are preferable.

The learning application unit 311 performs noise reduction processing on a medical image, which is to be subjected to the noise reduction processing, by applying the learned network based on the input image generated by the preprocessing unit 310. Here, the learned network is a program having a function similar to a function of outputting specific data with respect to input data. Therefore, in addition to that the learned network can be constructed by the calculation unit 130, the learned network can be constructed in advance by a calculation device provided separately from the calculation unit 130 and stored in the storage unit 140.

The X-ray CT apparatus configured as described above captures an image as follows. That is, the user inputs an imaging part, a tube voltage, a tube current amount, other imaging conditions, a viewing field size, image center, filter conditions, and other image generation conditions as imaging and image generation conditions by using the input unit 150, and gives an instruction to start imaging. The control unit 120 generates a control signal according to the input imaging conditions and outputs the control signal to the imaging unit 110.

The imaging unit 110 performs X-ray imaging according to the acquired control signal, and outputs a projection signal to the signal collection unit 131. The signal collection unit 131 converts the projection signal into a digital signal and outputs the digital signal to the image generation unit 132. The image generation unit 132 generates a reconstructed image (CT image), which shows an X-ray absorption coefficient of the subject, from the projection signal using an image reconstruction method, such as a Filtered Back Projection method or a sequential reconstruction method, according to the image generation conditions.

In the image processing unit 133, the preprocessing unit 310 acquires at least one of the digital projection signal collected by the signal collection unit 131 and the reconstructed image generated by the image generation unit 132, and generates an input image to be input to the leaned network by the learning application unit 311. The preprocessing unit 310 generates a plurality of input images as described above, and outputs these to the learning application unit 311. The learning application unit 311 reads the learned network stored in the storage unit 140, sets processing parameters required for the learned network, acquires an output image using the learned network based on the input image and outputs the output image.

(About Deep Learning Network)

Figure 3:
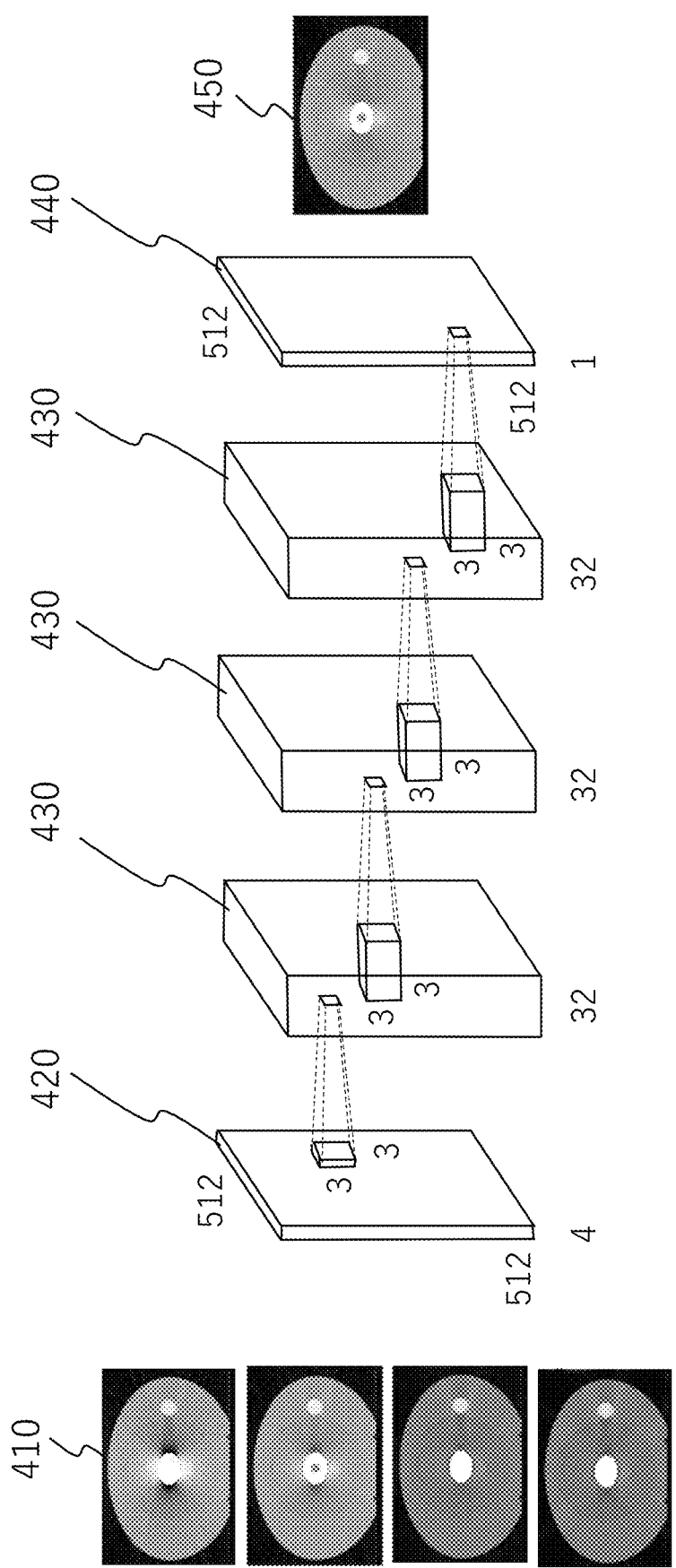
FIG. 3 is a reference diagram showing an example of the network structure of deep learning.

FIG. 3 shows an example of the structure of a deep learning network (hereinafter, simply referred to as a "network") used by the learning application unit 311.

In the present embodiment, the description will be given assuming that the learning application unit 311 uses a convolutional neural network (CNN) as a network. As shown in FIG. 3, the CNN includes an input layer 420 to which one or more images 410 including noise are input, a calculation unit 430 configured to repeat a large number of convolution operations, and an output layer 440 for outputting one noise-reduced image 450.

In FIG. 3, the numbers below blocks indicating the respective layers indicate the number of channels, the numbers within the respective layers indicate the sizes processed in the layers, and the numbers at the ends of the blocks indicating the input layer and the output layer indicate the sizes of the input and the output.

In the present embodiment, the network is a CNN that is widely used because of its superior processing accuracy and processing time. However, the network is not limited to the CNN, for example, MLP (Multi Layer Perceptron), VAE (Variational Auto Encoder), and GAN (Generative Adversarial Network) can be used.

(About Generation of Learning Data and Construction of Learned Network)

Hereinafter, the construction of the learned network applied by the learning application unit 311 will be described. In the present embodiment, as an example of the learned network applied by the learning application unit 311, as shown in FIG. 3, an image including noise caused by metal is input and a noise-reduced image is output using a CNN.

The learning data includes network input data and network output data (correct data). The input data and the output data form a pair, and the number of pairs is referred to as the number of pieces of data. In many cases, the number of pieces of data in deep learning is 100000 or more. In the following description, corresponding to a case where the network structure is exemplified as a CNN, input data, output data, and correct data are referred to as an input image, an output image, and a correct image, respectively.

Figure 4:
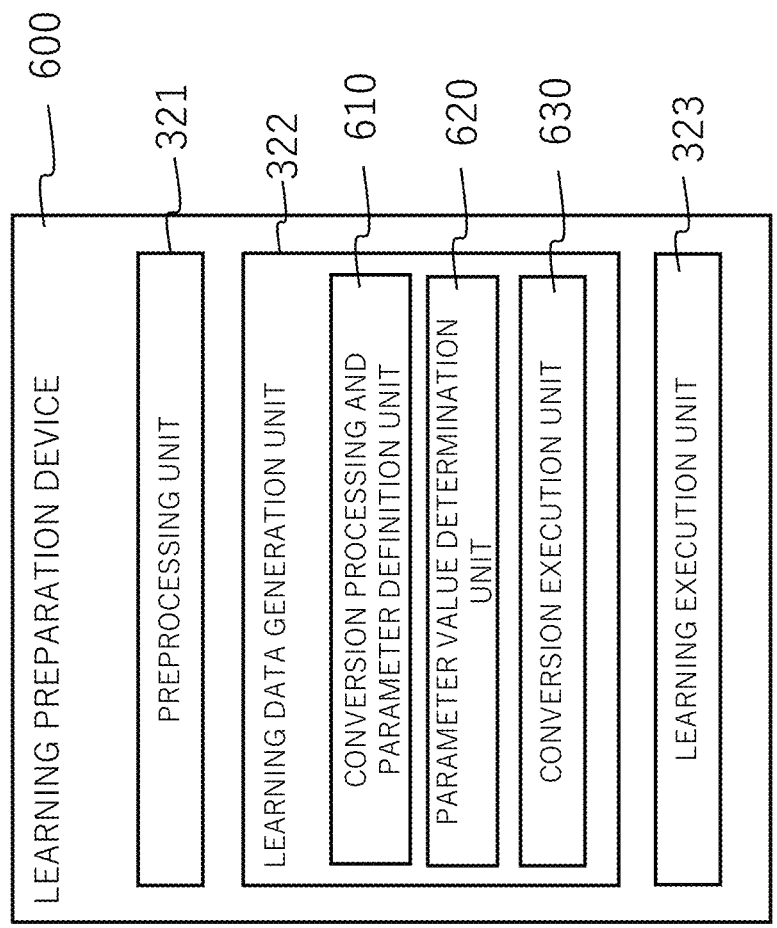
FIG. 4 is a reference block diagram showing a schematic configuration of a learning preparation device for generating learning data.

In the present embodiment, as shown in FIG. 4, in order to construct a learned network, learning data, that is, an input image and an output image (correct image) are generated by a learning preparation device 600. Not only can the learning preparation device 600 be provided in the calculation unit 130, but also a dedicated or general-purpose computer provided separately from the calculation unit 130 can be applied.

The learning preparation device 600 includes a preprocessing unit 321 that generates an input image, a learning data generation unit 322 that generates a correct image, and a learning execution unit 323 that causes a network to learn learning data.

The preprocessing unit 321 generates at least one noise-reduced image, which has been subjected to known noise reduction processing, in addition to the original image, as input images, similarly to the preprocessing unit 310 of the image processing unit 133. Specifically, similarly to the preprocessing unit 310, using a CT image as an original image, for example, three types of images of an output image as a noise-reduced image obtained by performing predetermined known first noise reduction processing on the original image, an intermediate image generated during the first noise reduction processing, and a noise-reduced image obtained by performing known second noise reduction processing on the original image are generated. The generated image may be temporarily stored in a storage device (not shown), or may be output to the learning data generation unit 322.

The learning data generation unit 322 includes a conversion processing and parameter definition unit 610, a parameter value determination unit 620, and a conversion execution unit 630.

The conversion processing and parameter definition unit 610 defines in advance conversion processing for converting an input image into an output image and parameters used in the conversion processing. In the present embodiment, since noise is reduced using a network, processing for obtaining a correct image with reduced noise for the input image is the conversion processing. For example, a weighted sum in a real space, a weighted sum in a frequency space, a combination thereof, or known noise reduction processing is appropriately selected. In addition, parameters used for the defined conversion processing are also defined.

The parameter value determination unit 620 specifically determines a parameter value for a parameter determined by the conversion processing and parameter definition unit 610. The conversion execution unit 630 converts the input image by applying the parameter value determined by the parameter value determination unit 620 to the conversion processing defined by the conversion processing and parameter definition unit 610, thereby generating an output image (correct image). In addition, the input image generated by the preprocessing unit 321 and the correct image generated by the learning data generation unit 322 may be stored in a storage device (not shown) as necessary.

The learning execution unit 323 collects learning data using the image generated by the preprocessing unit 321 as an input image and the correct image generated by the learning data generation unit 322 as an output image and applies the collected learning data to the CNN to perform iterative learning, thereby constructing a learned network.

(About Learning Data Generation Processing)

Figure 5:
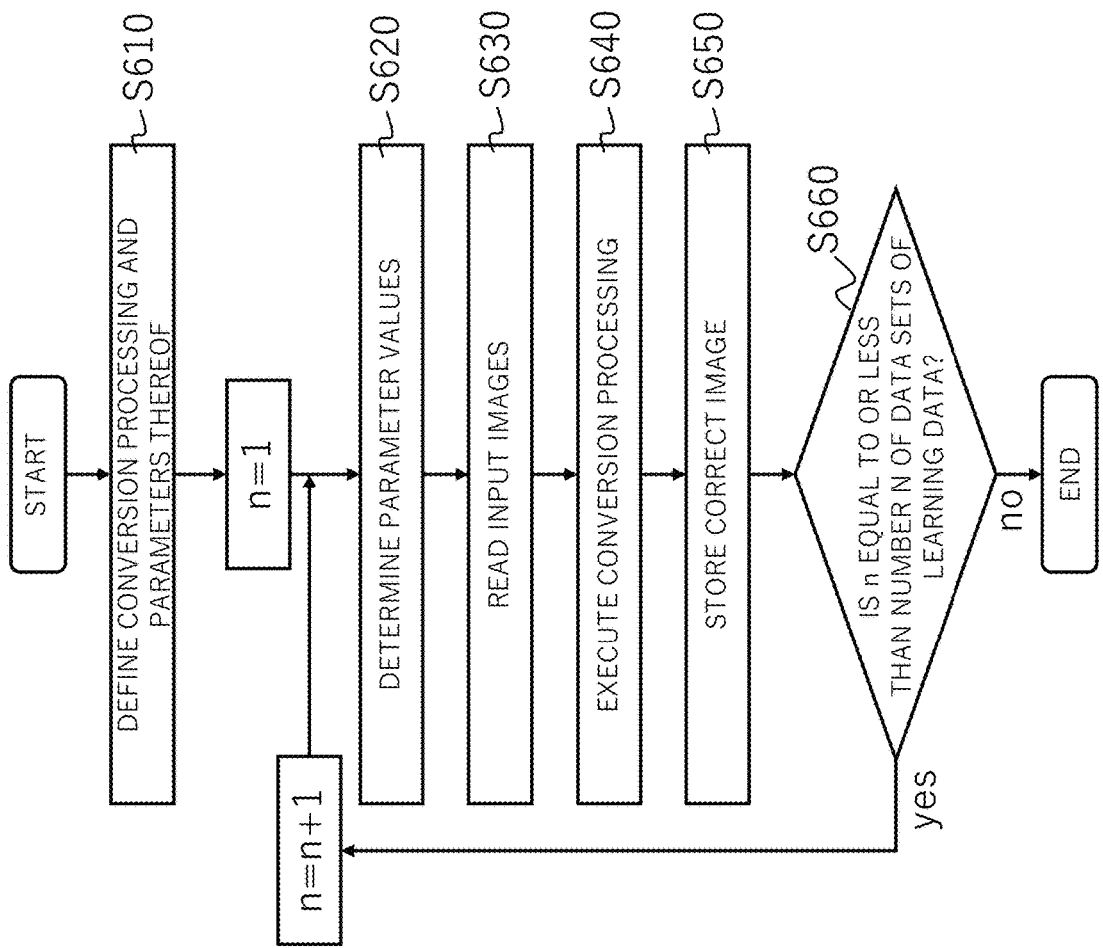
FIG. 5 is a flowchart according to a process of generating a correct image by the learning preparation device shown in FIG. 4.

Hereinafter, the flow of generating a correct image in the learning data generation unit 322 of the learning preparation device 600 configured as described above will be described with reference to the flowchart of FIG. 5.

When a program for implementing the learning data generation unit 322 is loaded and started, the learning data generation unit 322 realizes functions as the conversion processing and parameter definition unit 610, the parameter value determination unit 620, and the conversion execution unit 630. In step S610, the conversion processing and parameter definition unit 610 reads and defines conversion processing and parameters from a storage unit (not shown).

Thereafter, the first of processes for generating a number of correct images starts. In step S620, parameter values for obtaining a first correct image are set by the parameter value determination unit 620. Then, in step S630, the learning data generation unit 322 reads an input image for obtaining the first correct image from the preprocessing unit 321.

In the next step S640, the conversion execution unit 630 performs conversion processing on the input image using the parameter values set in step S620, and stores the obtained data as a correct image as a pair with the input image in a storage device (not shown) (step S650). When the number of pieces of data for generating the correct image is N, the operation from step S620 to step S650 is repeated N times (step S660), and the obtained data set is set as learning data.

In the present embodiment, an example has been described in which the parameter value is set to a different value depending on the input image. However, the parameter value may be a value common to all input images.

As described above, in the present embodiment, a learned network is constructed by using learning data having an image with noise as an input image and an image obtained by converting the input image as an output image. Therefore, for example, the learned network can also be applied to noise reduction processing on a medical image for which noise cannot be quantified by a general-purpose image quality evaluation index, such as an image for which a correct image cannot be obtained. Therefore, it is possible to accurately reduce noise and improve image quality.

In addition, it is preferable to construct a learned network in accordance with an image to be subjected to noise reduction processing or its noise. For example, when it is desired to reduce noise caused by metal, a learned network is constructed using learning data in which an image including noise caused by metal is an input image and an image with reduced noise caused by metal is an output image. By performing noise reduction processing using the learned network constructed in this manner, adaptive noise reduction processing can be performed for noise caused by metal, the noise having different definition depending on the purpose of the image and the noise being not able to be quantified with a general-purpose image quality evaluation index. As a result, a high noise reduction effect can be obtained.

More specifically, a learned network can be constructed using learning data having, as input images, two or more of an original image without noise reduction, a metal image having a value only in a metal region, a linear interpolation image obtained by linearly interpolating components affected by metal in a projection space, a beam hardening correction image in which noise caused by metal has been reduced by beam hardening correction processing, a high frequency image in which high frequency components of the original image are emphasized, an edge image showing the magnitude of the difference in pixel value between adjacent pixels in the original image, and a region divided image obtained by dividing a region according to the difference in the X-ray attenuation coefficient of the imaging target.

By performing the noise reduction processing using the learned network constructed using such learning data, it is possible to obtain a noise reduction effect more than the known noise reduction processing for noise caused by metal, the noise having different definition depending on the purpose of the image and the noise being not able to be quantified with a general-purpose image quality evaluation index.

Hereinafter, examples of learning data generation according to Examples 1 to 6 will be described.

<Example 1 of Learning Data Generation>

In this example, conversion processing for converting an input image defined by the conversion processing and parameter definition unit 610 into an output image is one of a weighted sum in a real space, a weighted sum in a frequency space, and a combination of the weighted sums in the real space and the frequency space. In addition, the parameter value determination unit 620 determines one or more values of the parameters used for converting the input image into the correct image based on the input by the user.

More specifically, when determining the parameter values, the learning data generation unit 322 reads the input images generated by the preprocessing unit 321 and displays the input images on a monitor or the like as an output device.

Figure 6:
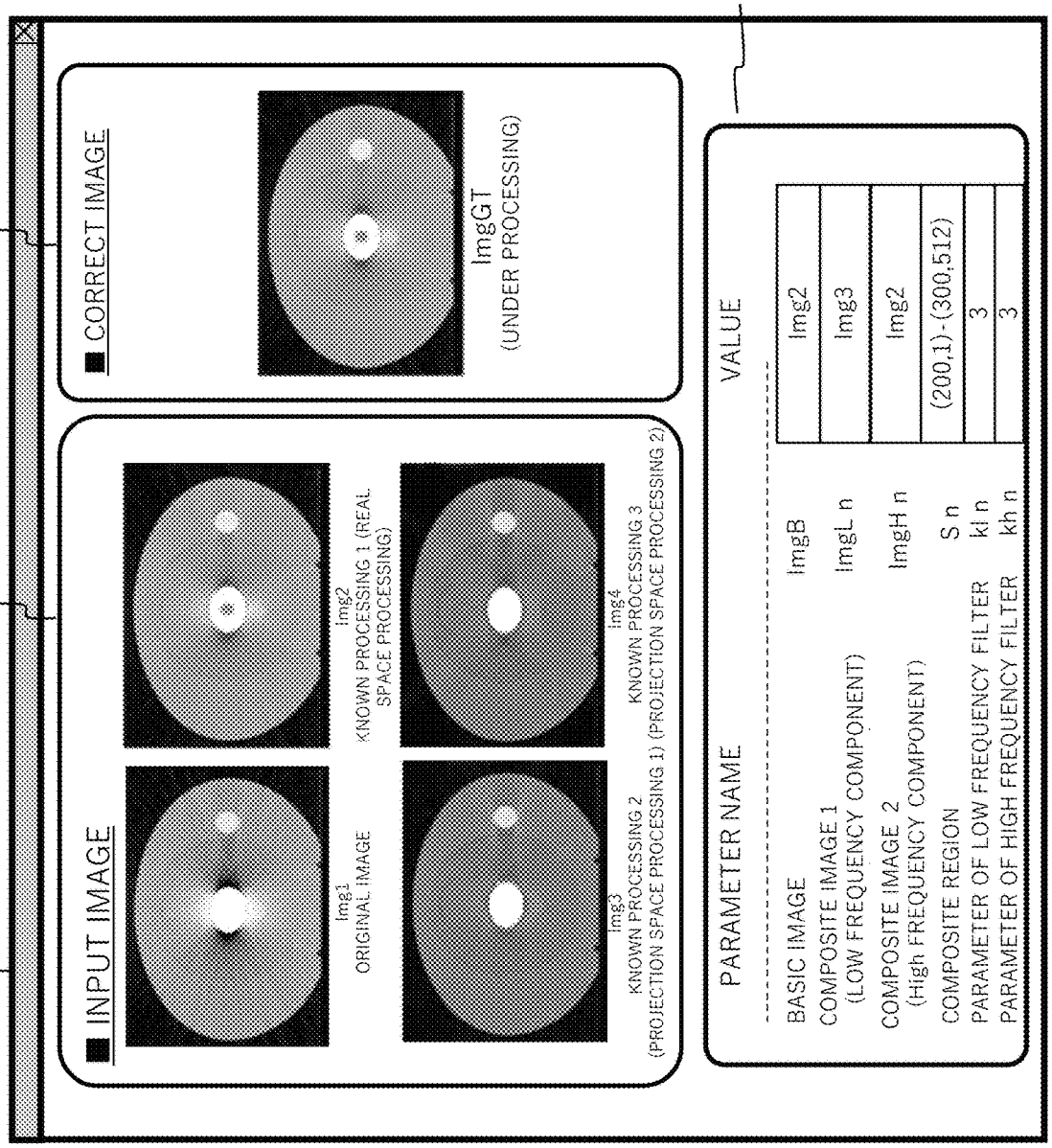
FIG. 6 is a reference diagram showing an example of a screen displayed on a monitor as an output device when determining a parameter value in Example 1 of learning data generation.

FIG. 6 shows an example of a screen displayed at this time. A screen 900 shown in FIG. 6 includes a display region 910 for displaying an input image, a parameter value input region 930 for inputting a conversion parameter, and a correct image display region 920 for displaying a correct image as a result of converting the input image using the input value parameter.

In the example shown in FIG. 6, parameters shown in the parameter value input region 930 are used, and a specific value can be input in the column on the right side of the parameter value input region 930. In the parameter value input region 930, a basic image (ImgB) loaded with a weighted sum 1 in a region not specified as a composite region in the real space, a composite image 1 (ImgLn) for mixing low frequency components, a composite image 2 (ImgHn) for mixing high frequency components, a composite region (Sn) that is a region for mixing a high frequency and a low frequency, a parameter (kln) of a low frequency filter for specifying a filter Kln for extracting low frequency components, and a parameter (khn) of a high frequency filter for specifying a filter Khn for extracting high frequency components are displayed as defined parameters.

In addition, processing for conversion from the input image (ImgHn, ImgHn, n=1, 2, ..., N) to the correct image (ImgGT), which is defined by the conversion processing and parameter definition unit 610, is a combination of weighted sums in the real space and the frequency space, and is conversion processing expressed by the following Equation (1).

[Equation 1]

$$ImgGT(i, j) = ImgB(i, j) + \sum_{n=1}^{N} S_n(i, j) \left\{ -ImgB(i, j) + \sum_{i',j'} ImgL_n(i, j)Kl_n(i-i', j-j') + ImgH_n(i, j)Kh_n(i-i', j-j') \right\} \quad (1)$$

In Equation (1), images, regions, and filters are all expressed by matrices having real values as components, i and j are row and column numbers corresponding to pixels, the suffix N is the number of regions to be combined, and n is an integer of 1 or more and N or less that numbers the regions.

More specifically, a case will be described in which an input image is an image with noise caused by metal and a correct image is an image with reduced noise caused by metal.

For example, the preprocessing unit 321 generates a total of four input images of an original image that is a CT image corresponding to an input image to be subjected to known noise reduction processing, a projection replacement image in which a component affected by metal is replaced in the projection space with a value that reduces the effect, a linearly interpolated image obtained by linearly interpolating the components affected by metal in the projection space, and a beam hardening correction image obtained by performing beam hardening correction processing.

The user visually determines, for example, an image having the least noise in most of the pixels among four input images with reference to the input image display region 910, and sets the image as the basic image (ImgB) in the parameter value input region 930. Then, a region where the signal of the low frequency component remains relatively well is visually determined in one of the four input images, and a region where the signal of the high frequency component remains relatively well is visually determined in another input image, and the regions are set as the composite region (Sn) in the parameter value input region 930.

FIG. 6 shows an example in which a region is specified in advance as a rectangle and x and y coordinates of two points specifying the rectangle are input as parameters. Then, in the parameter value input region 930, the user sets an image in which the signal of the low frequency component remains as the composite image 1 (ImgLn) and an image in which the signal of the high frequency component remains as the composite image 2 (ImgHn). In addition, by visually recognizing the spatial scale of the signal and noise in the composite image 1 and the composite image 2, a frequency suitable for the combination is determined, and the parameter (kln) specifying the low frequency filter and the parameter (khn) specifying the high frequency filter are set in the parameter value input region 930.

In this example, the filter shape for the low frequency filter is predetermined as a Gaussian filter, and the kernel size is used as a parameter. In addition, the high frequency filter is determined in advance as a filter obtained by subtracting the Gaussian filter from the identity map, and the kernel size of the Gaussian filter is used as a parameter. The parameter of the high frequency filter is preferably a value corresponding to the frequency of noise remaining in the composite image 2 from which high frequency components are extracted, for example, 3 or more and 7 or less.

When the parameter value is determined by the user, the result of converting the input image using the set parameter value is displayed in the correct image display region 920. The user may repeat a parameter value setting other than the setting of the basic image and visual recognition of the conversion result using the set parameter value by referring to the displayed conversion result. In Equation 1, N indicates the number of repetitions.

In the above example, for example, it is preferable that the basic image is a beam hardening correction image or a projection replacement image, the composite region is near a metal, the composite image 1 is a linear interpolation image, and the composite image 2 is a beam hardening correction image or a projection replacement image.

(About Learning Data Generation Processing)

Figure 7:
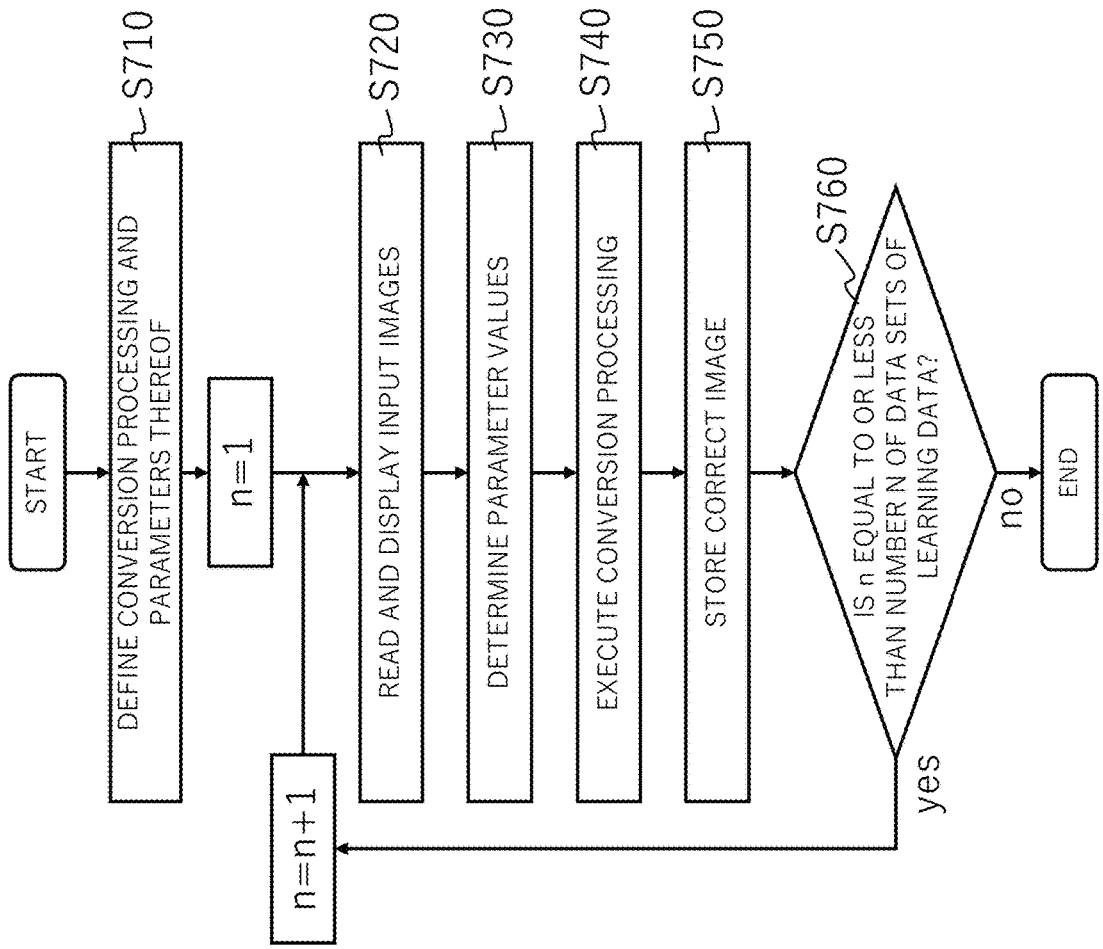
FIG. 7 is a process flowchart of learning data generation in Example 1 of learning data generation.

The processing for generating a correct image is specifically performed according to a flowchart shown in FIG. 7. Hereinafter, the flow of generating a correct image in the learning data generation unit 322 in Example 1 will be described with reference to the flowchart of FIG. 7.

When a learning data generation program is loaded and started, the learning data generation unit 322 realizes functions as the conversion processing and parameter definition unit 610, the parameter value determination unit 620, and the conversion execution unit 630. In step S710, the conversion processing and parameter definition unit 610 reads and defines conversion processing and parameters from a storage unit (not shown).

In step S720, the learning data generation unit 322 reads an input image for obtaining a correct image from the preprocessing unit 321, and displays the read input image on the monitor together with the parameters defined in step S710. In step S730, the value of each parameter is set by the parameter value determination unit 620 to obtain a correct image. Specifically, the user determines parameter values with reference to the input image displayed on the monitor, and inputs the values using an input device.

In the next step S740, the conversion execution unit 630 performs conversion processing on the input image using the parameter values set in step S730, and stores the obtained data as a correct image as a pair with the input image in a storage device (not shown) (step S750). When the number of pieces of data for generating the correct image is N, the operation from step S720 to step S750 is repeated N times (step S760), and the obtained data set is set as learning data.

In addition, in the above description, the processing for conversion processing from the input image to the correct image is a combination of the weighted sums in the real space and the frequency space. However, it is obvious that the processing becomes simpler when the parameters are set to extreme values. That is, setting one of the parameters of the low frequency filter and the high frequency filter to all pass and the other one to all cut-off becomes a process of replacing the composite region in the basic image with the composite image 1.

In addition, setting the composite region to the entire region of the image becomes an addition sum on the frequency. In addition, setting the parameter of the low frequency filter and the parameter of the high frequency filter so that their frequency distributions are different only by a constant multiple becomes an addition sum in the real space. Finally, setting one of the parameters of the low frequency filter and the high frequency filter to all pass and the other one to all cut-off and setting the composite region to the entire region of the image becomes a process of selecting one of the input images.

In addition, in the screen example of FIG. 6, an example is shown in which the parameter value input region 930 is a text box. However, the parameter value input region 930 may be realized as a GUI (Graphical User Interface) for selecting an image by clicking one of images displayed in the input information display region 910, or acquiring the coordinates of both end points of the composite region by clicking two points on the image, or acquiring filter parameters by inputting numbers to the standard output, or as a CUI (Character User Interface) for inputting numerical values or characters on a command line.

As described above, according to this example, the user determines and inputs one or more values of the parameters for the conversion from the input image to the correct image, and constructs a learned network using the result of the conversion processing using the input parameter values as a correct image and the input and output images as learning data. By using the learned network constructed in this manner, noise reduction processing can be performed with high accuracy even for noise that cannot be evaluated with a general-purpose image quality evaluation index.

In addition, the conversion processing defined by the conversion processing and parameter definition unit 610 is a combination of weighted sums in the real space and the frequency space. In particular, the input image is an image including noise caused by metal, and the learned network is constructed using output images after the projection replacement processing and the beam hardening correction processing, among the known noise reduction processes, as input images.

By applying such a learned network, a high noise reduction effect can be obtained. This is because the spatial distribution and the frequency distribution of the noise after the respective noise reduction processes are different, reflecting the difference between the principles of the projection replacement processing and the beam hardening correction processing among the known noise reduction processes.

In addition, by acquiring the parameters using the GUI, the time required to generate the correct image can be reduced.

<Example 2 of Learning Data Generation>

In this example, the conversion processing for converting an input image defined by the conversion processing and parameter definition unit 610 into an output image is conversion processing in which a part of known noise reduction processing is replaced with processing using parameters, and one or more values of the parameters are determined based on the input by the user.

In this example, an example will be described in which known noise reduction processing used in the conversion processing is processing in the projection space. Here, as the processing in the projection space, a plurality of processes such as NMAR (Normalized metal Artifact reduction), O-MAR (Orthopedic-Metal Artifact Reduction), and SEMAR (Single Energy Metal Artifact Reduction) are known, and each of these includes largely three processing elements.

That is, the first processing element is region division processing in which the original image is divided into regions, such as air, soft tissue, and bone tissue, to obtain a region divided image. In addition, the second processing element is region-specific noise reduction processing in which a noise component in each region is reduced by setting the region of the air in the original image to 0 HU, setting the region of the soft tissue to 1000 HU, and setting the region of the bone tissue to the original CT value+1000 HU, thereby obtaining a region-specific noise-reduced image. In addition, the third processing element is metal portion replacement processing in which projection processing is performed on the region-specific noise-reduced image and the original image, a projection value affected by metal in the projection image of the original image is replaced with a projection value of the region-specific noise-reduced image, and then back projection is performed to obtain a corrected image.

In this example, among the three processing elements, the region-specific noise reduction processing, that is the second processing element is replaced with processing using parameters.

Hereinafter, conversion processing for generating a correct image from an input image by the learning data generation unit 322 in this example will be described with reference to the flowchart of FIG. 8.

In this example, four input images, which are to be input to generate a correct image, are generated. Before the generation of the correct image by the learning data generation unit 322, the preprocessing unit 321 generates a total of four images of the original image, images (known reduction-processed image 1 and known reduction-processed image 2) obtained by performing known noise reduction processes of different methods on the original image, and a high frequency image.

Figure 8:
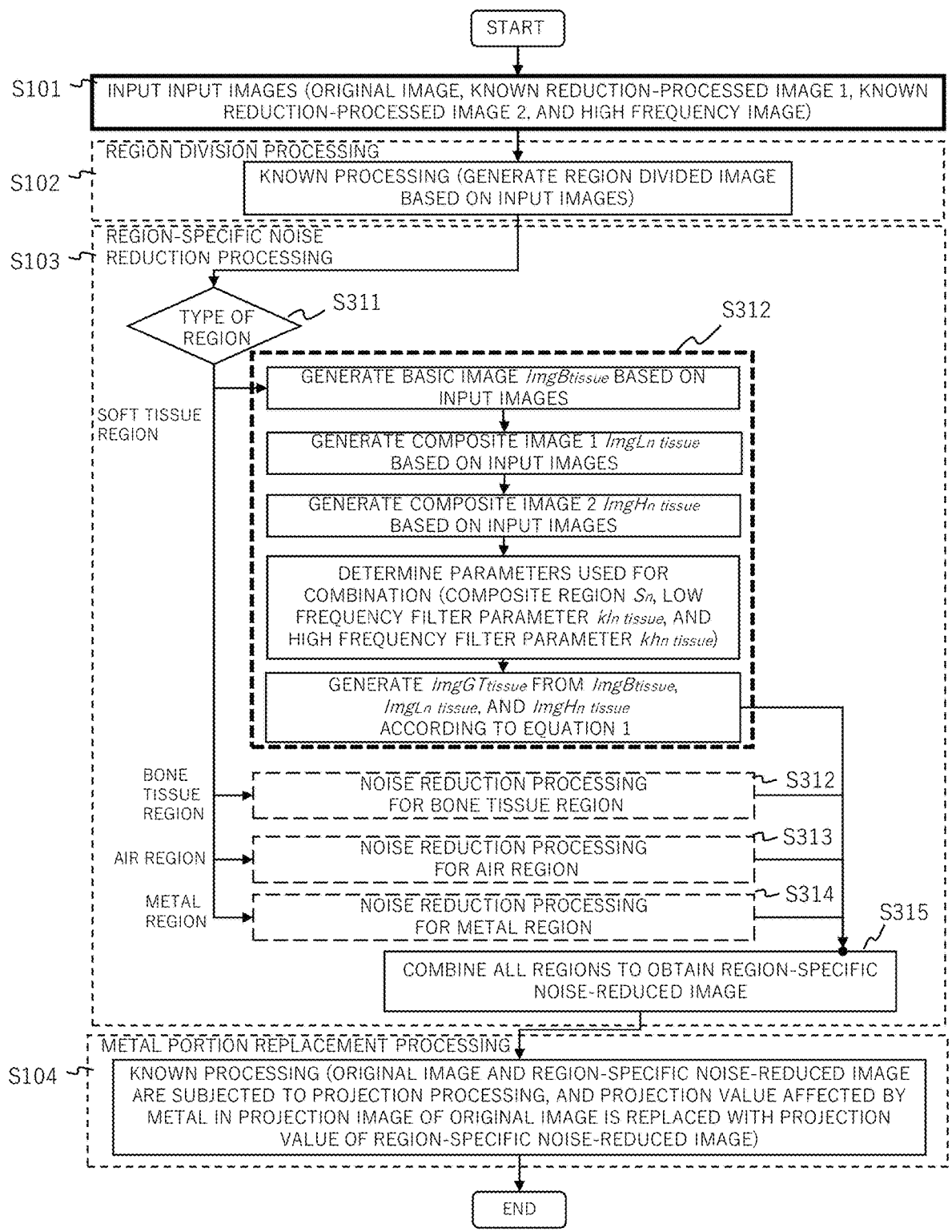
FIG. 8 is a process flowchart of learning data generation in Example 2 of learning data generation.

In step S101 in FIG. 8, the four input images generated by the preprocessing unit 321 are input to the learning data generation unit 322. In the next step S102, the conversion execution unit 630 performs region division processing for dividing the four images into regions, such as air, soft tissue, and bone tissue, to generate a region divided image.

Subsequently, in the next step S103, noise reduction processing suitable for each region is performed on the region divided image to generate a region-specific noise-reduced image.

More specifically, for the region divided image obtained from the four input images, different processing is performed for each region in step S311, thereby performing processing for each region. Specifically, noise reduction processing for the soft tissue region is performed in step S312, noise reduction processing for the bone tissue region is performed in step S313, noise reduction processing for the air region is performed in S314, and noise reduction processing for the metal region is performed in S315.

Here, the noise reduction processing for the soft tissue region in step S312 will be described.

In the noise reduction processing in step S312, a part of the known noise reduction processing is replaced with processing using parameters. That is, the noise reduction processing for the soft tissue region and the input image corresponding thereto are different from the known noise reduction processing.

Specifically, in the known noise reduction processing, all the soft tissue regions are set to a fixed value, for example, 1000 HU. However, in the noise reduction processing for soft tissue in this example, a basic image is specified and a composite image 1 (low frequency component) is generated and a composite image 2 (high frequency component) is generated, and a composite region, a low frequency filter, and a high frequency filter are specified and noise reduction processing is performed on the soft tissue region by performing combination using Equation (1).

The parameters are the basic image, the composite image 1, the composite image 2, the composite region, the parameters of the low frequency filter, and the parameters of the high frequency filter, as in Example 1.

For example, the parameter values are as follows: the known reduction-processed image 1 is a linear interpolation image, the known reduction-processed image 2 is a beam hardening correction image, the basic image and the composite image 2 are beam hardening correction images, the composite image 1 is a linear interpolation image, the composite region is the entire region, the low frequency filter is a Gaussian kernel having a kernel size of 3, and the high frequency filter is a filter obtained by subtracting the low frequency filter from the identity conversion.

The noise reduction processing images of respective regions of the soft tissue region, the bone tissue region, the air region, and the metal region obtained in step S312 are combined to generate a region-specific noise-reduced image (step S315).

In the next step S104, a portion affected by the metal in the projection image of the original image is replaced with a projection image of the region-specific noise-reduced image obtained as described above, and an image in which noise is reduced by back projection is generated. In this example, the image with reduced noise obtained as described above is a correct image.

As described above, parameters are often generated when processing is complicated for high accuracy, but a method for optimizing parameters is not obvious. However, according to this example, since the parameters are determined and set by the user, high-accuracy processing is possible. As a result, a correct image with less noise can be obtained.

<Example 3 of Learning Data Generation>

In Example 2, the noise reduction processing for soft tissue (S312) is region-specific noise reduction processing using parameters, and the result of performing the metal portion replacement processing is a correct image.

In general, in image processing in which a plurality of image processes are included and an intermediate image is generated, the target image quality of the intermediate image may be different from the target image quality of the final output. Since some of high frequency components, such as the texture of the image, are recovered by the metal portion replacement processing, the accuracy of the low frequency components is important in the region-specific noise reduction processing. For this reason, in this example, the accuracy of the composite image 1 that is a low frequency component of the correct image in Example 2 is further improved.

Figure 9:
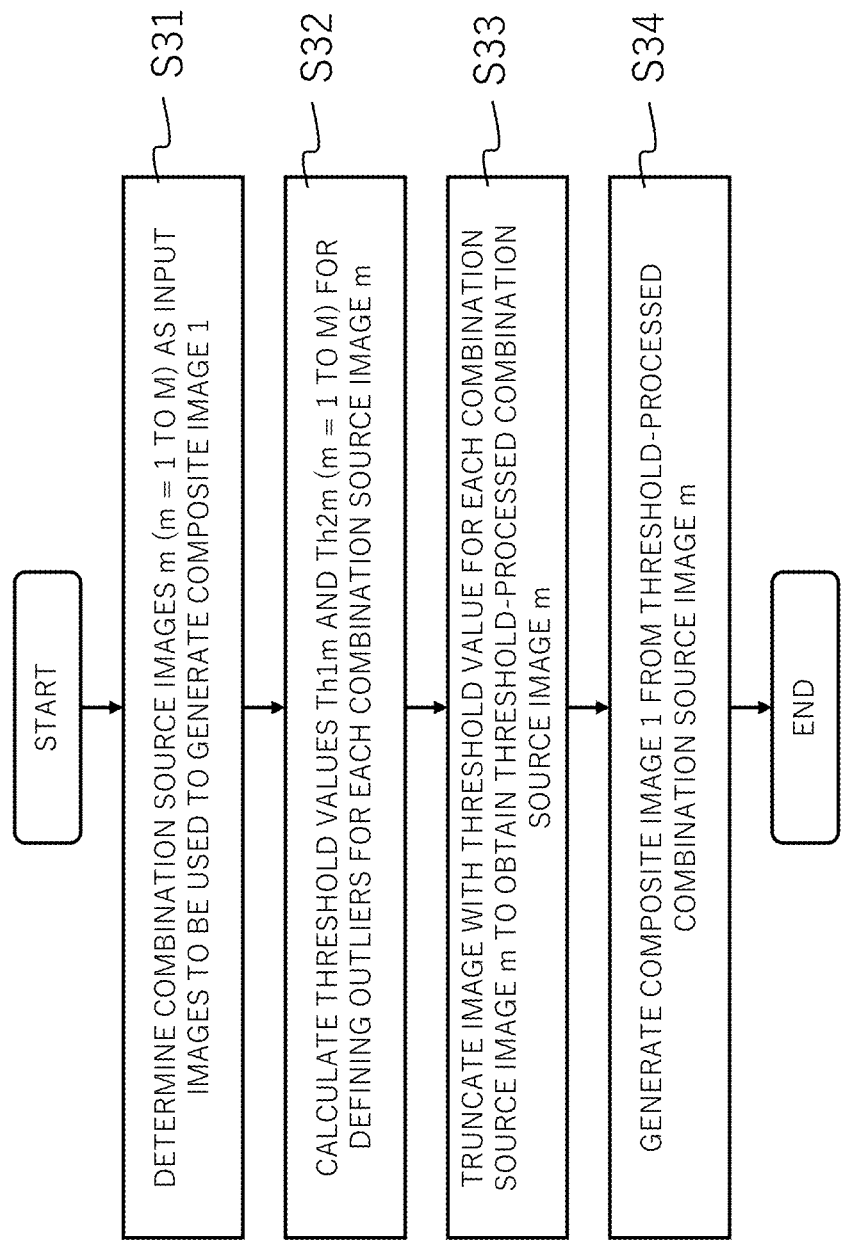
FIG. 9 is a process flowchart of learning data generation in Example 3 of learning data generation.

In the following description, another example of the processing for generating the composite image 1 in the noise reduction processing for the soft tissue region in this example, that is, in the region-specific noise reduction processing (S103) in Example 2, will be described with reference to the flowchart of FIG. 9.

The composite image 1 in this example is generated from a plurality of input images instead of selecting one of the input images. Therefore, first, M input images to be used to generate the composite image 1 are determined, and are set as combination source images m (m=1 to M) (step S31). Here, it is desirable that the combination source images m are input images that include low frequency components and have different noise characteristics. For example, in the case of M=2, it is preferable that the combination source image 1 is a beam hardening correction image and the combination source image 2 is a linear interpolation image.

Then, in step S32, threshold values Th1$m$ and Th2$m$ for defining outliers are calculated for each combination source image m. For example, the threshold values are determined based on the average value and the variance of the CT values in the soft tissue region.

As an example, a threshold value in the case of a beam hardening correction image and a linear interpolation image will be described. In the case of the beam hardening correction image, since the remaining noise is noise that can be separated from the signal to some extent by the distribution of CT values and can be further reduced by the metal portion replacement processing, some remaining noise may be allowed. Therefore, it is preferable that the threshold values Th11 and Th21 of the combination source image 1 is the average value±variance/2 of the combination source image 1.

On the other hand, in the case of the linearly interpolated image, it is not preferable to allow the remaining noise in the image, contrary to the case of the beam hardening correction image. For this reason, it is necessary to reduce noise even at the expense of loss of signal, and the threshold values Th12 and Th22 of the combination source image 2 are preferably the average value±variance/5 to the average value±variance/3 of the combination source image 2.

Subsequently, in the next step S33, the combination source image m is truncated with the threshold value Th1$m$ of the combination source image as the lower limit and the threshold value Th2m as the upper limit, thereby obtaining a threshold-processed combination source image m. Finally, in step S34, the composite image 1 is generated from the threshold-processed combination source image m. As a method of combining the threshold-processed combination source image m into the composite image 1, for example, a combination method is preferable in which pixels that are not outliers of the combination source image 1 have pixel values of the combination source image 1, pixels that are not outliers of the combination source image 2 other than the above pixels have pixel values of the combination source image 2, and pixels other than these pixels have pixel values of the threshold-processed combination source image 1.

As described above, when the frequency distribution of noise depends on the imaging target, the user can determine and set the optimal parameters to generate an intermediate image in which low frequency components are well reproduced. By constructing the learned network using the correct image obtained based on this, it is possible to improve the noise reduction rate in the noise reduction processing using the learned network.

<Example 4 of Learning Data Generation>

In this example, a different method is used for the noise reduction processing (S313) for the bone tissue region in Example 2 or 3. In the known noise reduction processing for the bone tissue region in Example 2 or 3, the value of the original image is used as a region-specific noise-reduced image. In this example, however, among the input images, the original image, the known reduction-processed image 1 and the known reduction-processed image 2 are compared for each pixel, and the maximum value of the three images for all pixels is set as a pixel value. In this case, the parameter is a variable that specifies an image having a pixel indicating the maximum value, for example, the original image, the known reduction-processed image 1, and the known reduction-processed image 2.

Noise caused by metal tends to reduce the pixel value of bone tissue. Therefore, when the spatial distribution of noise differs depending on the type of known reduction processing, an effect of recovering the reduction of the pixel value in the bone tissue of the generated correct image can be obtained by applying this example, in which the maximum value of the original image and the known reduction processing is adopted, for each pixel. Thus, by constructing a learned network using a correct image in which the noise reduction rate of the bone tissue region has been improved by the noise reduction processing reflecting the characteristic of the noise in the bone tissue and by applying the learned network to the noise reduction processing, it is possible to improve the noise reduction rate.

<Example 5 of Learning Data Generation>

In Examples 2 to 4, the region-specific noise reduction processing has been performed with high accuracy. However, the region division processing or the metal portion replacement processing may be performed with high accuracy.

It is considered that the high-accuracy processing of the region division processing is realized by, for example, a combination of edge detection processing and morphology processing. The parameters set by the user include selection of edge detection methods such as the Sobel method, Gaussian Nora Placian method, and Canny method, parameters for each edge detection method such as two threshold values in the case of the Canny method, and parameters of morphology processing.

Since the user determines and sets the parameters of each process as described above, even when there is a factor that greatly changes the optimal value of the parameter, for example, there is noise whose intensity or spatial pattern depends on the imaging target, the region division processing can be performed with high accuracy, and an appropriate correct image can be generated. Therefore, by constructing a network using the correct image and using the network for noise reduction processing, it is possible to improve the image quality by accurately reducing noise even for a medical image for which noise cannot be quantified by a general-purpose image quality evaluation index.

<Example 6 of Learning Data Generation>

In Examples 2 to 5, among the processes for reducing noise caused by metal, some of the processes in the projection space have been performed with high accuracy. However, some of the iterative processes of the combination of the processing in the real space, such as the beam hardening correction processing, and the processing in the real space and the projection space, such as sequential reconstruction, may be performed with high accuracy.

For example, in the case of performing the beam hardening correction processing with high accuracy, a region where beam hardening is likely to occur is detected by the beam hardening correction processing, and an error image is generated. When mounting is performed by processing of subtracting i times the error image from the original image with i as a constant, i is the parameter.

As described above, since the user determines and sets the parameters of the processing, it is possible to acquire a correct image with reduced noise with high accuracy even for noise that can be visually recognized but cannot be quantified by a general-purpose image quality index. Therefore, by constructing a network using the correct image and using the network for noise reduction processing, it is possible to improve the image quality by accurately reducing noise even for a medical image for which noise cannot be quantified by a general-purpose image quality evaluation index.

Second Embodiment

In the present embodiment, the image processing unit 133 of the X-ray CT apparatus recognizes the purpose of the input image and performs noise reduction processing according to the purpose. Here, the purpose of the image is specified by an imaging part, such as a head, a jaw, a chest, an abdomen, a lumbar spine, and a hip joint, and an imaging tissue, such as a soft tissue and a bone tissue. When the imaging tissue is a soft tissue, the CT image is used for diagnosis of a soft tissue disease, such as an internal disease or a malignant tumor. When the imaging tissue is a bone tissue, the CT image is used for diagnosis of an orthopedic disease, such as a fracture.

Figure 10:
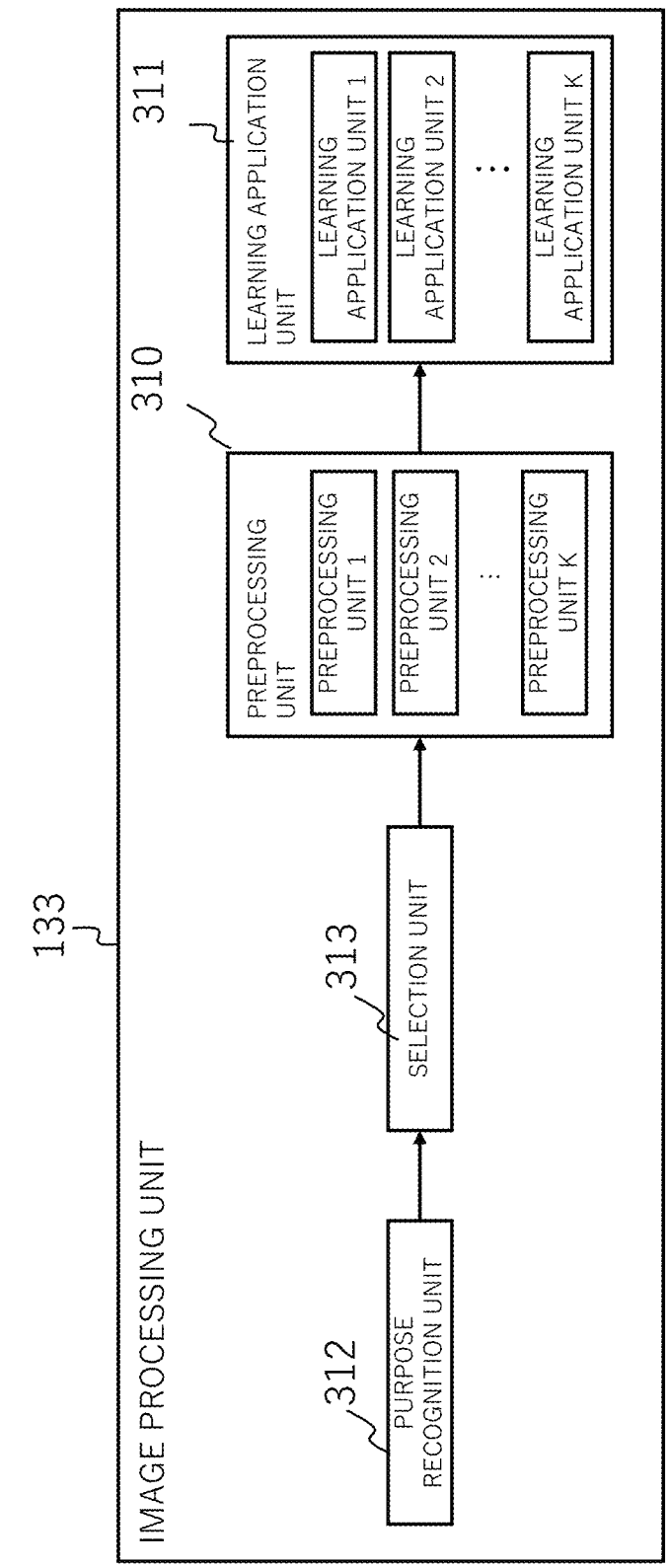
FIG. 10 is a block diagram showing a schematic configuration of an image processing unit (image processing apparatus) according to a second embodiment of the invention.

For this reason, as shown in FIG. 10, the image processing unit 133 in the present embodiment includes a plurality of (for convenience of explanation, K in the present embodiment) preprocessing units and learning application units provided for each purpose, a purpose recognition unit 312 for recognizing the purpose of the input image, and a selection unit 313 for selecting an appropriate preprocessing unit and learning application unit from the plurality of preprocessing units and a plurality of learning application units according to the recognition result of the purpose recognition unit 312.

In the K preprocessing units 310 and the K learning application units 311, a preprocessing unit k calculates an input image with respect to a learning application unit k (hereinafter, k is referred to as a "conversion number", and k=1 to K). In addition, the learning application unit k is associated with the purpose or a learned network appropriate for performing noise reduction processing corresponding to the purpose. Therefore, when the preprocessing unit and the learning application unit are selected by the selection unit 313 according to the purpose recognized by the purpose recognition unit 312, an input image corresponding to the purpose is generated, and noise reduction processing is performed by applying an optimal learned network.

The conversion number k is associated in advance with the purpose and a learned network appropriate for performing noise reduction processing corresponding to the purpose, and the preprocessing unit and the learning application unit with the same conversion number k all have a correspondence relationship therebetween. FIG. 11 shows a correspondence table showing an example of the correspondence relationship between a series of processes represented by k and the purpose.

In FIG. 11, K is 12. For example, the conversion number 1 indicates a diagnosis of the bone tissue of the head, the preprocessing unit 310 associated with the conversion number 1 generates an input image corresponding thereto, and a learned network for performing noise reduction processing appropriate for the image of the bone tissue is associated with the head of the learning application unit associated with the conversion number 9. The same applies to the following conversion numbers.

In addition, the purpose and the conversion number do not need to correspond to each other in a one-to-one manner. As shown in the example of the hip joint of the conversion number 9 in FIG. 11, when the same noise reduction processing is effective for the bone tissue and the soft tissue, the same processing may be performed. Therefore, the bone tissue and the soft tissue can be associated with the same conversion number. In addition, as shown by the conversion numbers 10 and 11, even in a case where the imaging parts are different such as the case of the knee and the shoulder, the imaging parts can be associated with the same conversion number when the same noise reduction processing is effective. A data table indicating the correspondence between the purpose and the conversion number is stored in a storage unit (see FIG. 1) in advance.

The flow of noise reduction processing when a plurality of preprocessing units and a plurality of learning application units are provided as described above will be described with reference to the flowchart of FIG. 12.

In step S41, when an original image is input from the image generation unit, the purpose recognition unit 312 identifies the purpose of the original image and outputs the purpose to the selection unit 313. In the next step S42, the selection unit 313 reads a data table showing a correspondence relationship between the purpose and the conversion number from the storage unit 140, and outputs the conversion number k corresponding to the purpose acquired from the purpose recognition unit 312 to the preprocessing unit 310.

In step S43, the preprocessing unit 310 executes processing, which is associated with the preprocessing unit k corresponding to the conversion number k, to calculate an input image of the learning application unit k, and outputs the input image to the learning application unit k. In step S44, the learning application unit k outputs an image in which noise has been reduced from the input image acquired by applying the learned network associated with the learning application unit k, and ends the process.

Here, for example, the purpose recognition unit 312 can perform processing for reading an image input from the image generation unit 132 and specifying the imaging part by performing image recognition on the image to recognize the shape of the imaging target, or specifying the imaging tissue by recognizing the frequency components of the imaging target, or specifying the purpose from the imaging part and the imaging tissue.

In addition, the purpose may be specified using the image generation conditions input by the input unit 150 together. Of the image generation conditions, for example, the image reconstruction filter has a correspondence relationship with the imaging tissue since the bone tissue is usually a high pass filter and the soft tissue is usually a low pass filter. Therefore, the imaging tissue can be specified from the reconstruction filter.

As described above, according to the present embodiment, by using a plurality of learned networks according to the purpose of the image, it is possible to perform noise reduction processing corresponding to the purpose of the image. Therefore, even for a medical image in which the definition of noise and signal differs depending on the purpose of the image, a higher noise reduction effect can be obtained.

What is claimed is:

1. An image processing apparatus, comprising:
   a preprocessing unit which includes a noise reduction processing unit; and
   a learning application unit that applies a learned network to perform noise reduction processing of an original image,
   wherein the preprocessing unit outputs the original image to the learning application unit as a first input image among a plurality of input images input to the learning application unit,
   wherein the noise reduction processing unit generates a plurality of second input images among the plurality of input images to be input to the learning application unit by performing preprocessing noise reduction processing on the original image to obtain the plurality of second input images,
   wherein the learning application unit performs the noise reduction processing of the original image based on the plurality of input images including the first input image and the plurality of second input images,
   wherein the learned network is constructed by performing deep learning using a plurality of learning sets of the plurality of input images which include two or more of the original image, a metal image having a value only in a metal region, a linear interpolation image obtained by linearly interpolating components affected by metal in a projection space, a beam hardening correction image in which noise caused by metal has been reduced by beam hardening correction processing, a high frequency image in which high frequency components of the original image are emphasized, an edge image showing a magnitude of a difference in pixel value between adjacent pixels in the original image, and a region divided image obtained by dividing a region according to a difference in X-ray attenuation coefficient of an imaging target, and
   wherein the learned network generates a correct image, which is obtained based on the plurality of input images and in which noise caused by metal has been reduced, as an output image.

2. The image processing apparatus according to claim 1, wherein the correct image is obtained by performing, on the input images, any processing of a weighted sum in a real space, a weighted sum in a frequency space, and a combination of the weighted sums in the real space and the frequency space.

3. The image processing apparatus according to claim 1, wherein the correct image is obtained by performing known noise reduction processing on the input images in a state in which a value of a predetermined parameter used for processing has been specified by a user.

4. An image processing method, comprising:
a preprocessing step for outputting an original image as a first input image among a plurality of input images to be input to a learning application unit;
a noise reduction processing step for generating a plurality of second input images among the plurality of input images to be input to a learning application unit by performing preprocessing noise reduction on the original image to obtain the plurality of second input images;
applying, by the learning application unit, a learned network to perform noise reduction processing of the original image based on the plurality of input images,
wherein the learned network is constructed by performing deep learning using a plurality of learning sets in which two or more of the original image, a metal image having a value only in a metal region, a linear interpolation image obtained by linearly interpolating components affected by metal in a projection space, a beam hardening correction image in which noise caused by metal has been reduced by beam hardening correction processing, a high frequency image in which high frequency components of the original image are emphasized, an edge image showing a magnitude of a difference in pixel value between adjacent pixels in the original image, and a region divided image obtained by dividing a region according to a difference in X-ray attenuation coefficient of an imaging target, and
generating a correct image using the learned network, which is obtained based on the plurality of input images and in which noise caused by metal has been reduced, as an output image.

5. An X-ray CT apparatus, comprising:
an imaging unit that emits X-rays to a subject and detects X-rays transmitted through the subject to generate an image; and
the image processing apparatus according to claim 1,
wherein the image processing apparatus performs noise reduction processing using the image generated by the imaging unit as the original image.

* * * * *